United States Patent

Boyle et al.

[11] 4,053,615
[45] Oct. 11, 1977

[54] PHTHALIMIDOPIPERIDINES AND ANTI-CONVULSANT COMPOSITIONS THEREOF

[75] Inventors: John Terence Arnott Boyle; John Christopher Saunders, both of Maidenhead, England

[73] Assignee: John Wyeth & Brother Limited, Maidenhead, England

[21] Appl. No.: 650,828

[22] Filed: Jan. 21, 1976

Related U.S. Application Data

[63] Continuation-in-part of Ser. No. 543,397, Jan. 23, 1975, abandoned, which is a continuation-in-part of Ser. No. 405,332, Oct. 11, 1973, abandoned.

[30] Foreign Application Priority Data

Oct. 21, 1972 United Kingdom .............. 48594/72
Jan. 23, 1975 United Kingdom ................ 2923/75

[51] Int. Cl.$^2$ ........................................... C07D 401/04
[52] U.S. Cl. ............................... 424/267; 260/293.61; 260/293.77; 260/287 AR
[58] Field of Search .................... 260/293.61; 424/267

[56] References Cited

U.S. PATENT DOCUMENTS 3,316,276  4/1967  Helsley ................................. 260/326

*Primary Examiner*—Henry R. Jiles
*Assistant Examiner*—Richard A. Schwartz
*Attorney, Agent, or Firm*—Arthur E. Wilfond

[57] ABSTRACT

Phthalimidopiperidines of the formula

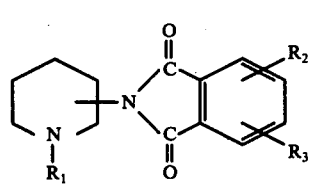

(I)

are described where $R_1$ is hydrogen, lower alkyl, cycloalkyl of 5 to 7 carbon atoms, phenyl(lower)alkyl, pyridyl(lower)alkyl, furyl(lower)alkyl or thienyl(lower)alkyl and $R_2$ and $R_3$ are hydrogen or various substituents. The compounds are useful pharmaceutically, particularly as anti-convulsants, and also in some cases as anti-arrhythmic agents and anti-inflammatory agents, and in some cases useful as intermediates for the preparation of 4-aminoquinoline derivatives having anti-malarial activity.

21 Claims, No Drawings

PHTHALIMIDOPIPERIDINES AND ANTI-CONVULSANT COMPOSITIONS THEREOF

The present application is a continuation-in-part of Application Ser. No. 543,397, now abandoned entitled "Piperidine Derivatives" and filed on 23 Jan. 1975 in the name of John Terence Arnott Boyle and John Christopher Saunders. Application Ser. No. 543,397 is in turn a continuation-in-part of Application Ser. No. 405,332, now abandoned, entitled "Piperidine Derivatives and filed on 11 Oct. 1973 in the name of John Terence Arnott Boyle and John Christopher Saunders.

The present invention relates to novel phthalimidopiperidine derivatives, a process for their manufacture and pharmaceutical compositions containing them.

The invention presents new compounds of the formula

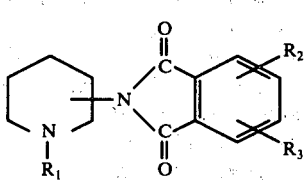
(I)

and their pharmaceutically acceptable acid addition salts, wherein $R_1$ is selected from the group consisting of hydrogen, lower alkyl, cycloalkyl of 5 to 7 carbon atoms, phenyl(lower)alkyl, pyridyl(lower)alkyl, furyl(lower)alkyl and thienyl(lower)alkyl, and $R_2$ and $R_3$ are independently selected from the group consisting of hydrogen, halogen, lower alkyl, nitro, amino and di(-lower alkyl)amino.

The term "lower" as used herein denotes that the alkyl group contains up to 6 carbon atoms, preferably up to 4 carbon atoms.

As illustrative examples of lower alkyl represented by $R_1$ there may be mentioned methyl, ethyl, n-or i-propyl, n-butyl and n-hexyl. $R_1$ may also represent cycloalkyl of 5 to 7 carbon atoms, in particular, cyclopentyl, cyclohexyl and cycloheptyl, preferably cyclohexyl. $R_1$ may also represent phen(lower)alkyl, particularly, benzyl, phenylethyl, phenylpropyl and the like. As pyridyl(-lower)alkyl there may be mentioned pyridylmethyl and pyridylethyl. As furyl(lower)alkyl there may be mentioned furylmethyl, particularly furfuryl, and furylethyl. As thienyl(lower)alkyl there may be mentioned thienylmethyl and thienylethyl.

$R_2$ and $R_3$, which may be the same or different, each represent hydrogen, halogen (for instance, chlorine or bromine), lower alkyl (for instance, methyl, ethyl, i- or n-propyl or n-butyl), nitro, amino or di(lower alkyl-)amino (for instance dimethylamino or diethylamino).

The acid addition salts may be formed from inorganic and organic acids. Examples of pharmaceutically acceptable acid addition salts include the sulphate, hydrochloride, hydrobromide, hydroiodide, nitrate, phosphate, sulphonate (such as the methanesulphonate and p-toluene-sulphonate), acetate, maleate, fumarate, tartrate, malonate, citrate and formate.

Some of the compounds according to the invention possess an asymmetric carbon atom, for example, when the phthalimido or substituted phthalimido group substitutes the 3-position of the piperidine ring. For instance, the compound 1-benzyl-3-phthalimidopiperidine of formula

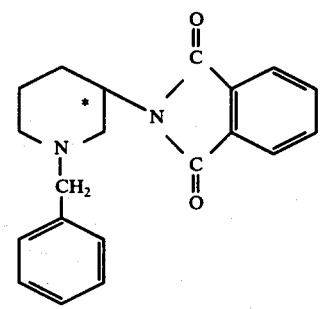
(II)

possesses an asymmetric carbon atom at the position marked with an asterisk in formula II. It is to be understood that the compounds of the invention include the enantiomers of the compounds with an asymmetric carbon atom and mixtures of the enantiomers, for example, racemic mixtures of the enantiomers. General methods of separation of enantiomers are recorded in the literature.

The compounds of formula I and their acid addition salts may be prepared by building up the molecule from appropriate starting materials by known reactions. In particular the phthalimido group or substituted phthalimido group may be introduced by reaction of an amino-substituted piperidine with a reactive derivative of phthalic acid or substituted phthalic acid.

The invention provides a process of preparation of a compound according to formula I or an acid addition salt thereof, in which a. a compound of formula

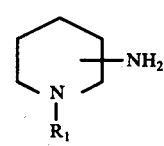
(III)

(where $R_1$ is as defined above) or a corresponding compound with a protecting group is reacted with a reactive derivative of an acid whose formula is

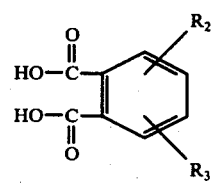
(IV)

(where $R_2$ and $R_3$ are as defined above), the reactive derivative being, for example, phthalic anhydride or its substitution product, or b. a compound of formula

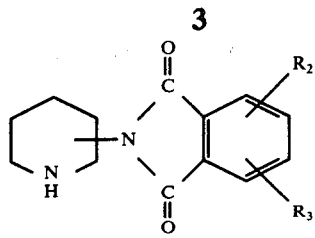
(V)

where $R_2$ and $R_3$ are identified above, is subjected to alkylation (where the alkyl group introduced may be substituted by a phenyl, pyridyl, furyl or thienyl group) to form a compound of formula I where R denotes lower alkyl, phenyl(lower)alkyl, pyridyl(lower)alkyl, furyl(lower)alkyl or thienyl(lower)alkyl group. If necessary or desired, the process may also include removal of a protecting group and, if desired, conversion of an acid addition salt of product, of formula I into its free base form or conversion of the free base form of a product of formula I into an acid addition salt form.

Where a final product is desired in which $R_1$ is hydrogen, it is expedient to use an aminopiperidine starting material for step (a) with a protecting group instead of the said hydrogen atom in order to avoid any possible reaction of the phthalic acid derivative at the piperidine ring nitrogen atom. For example, a benzyl group may be used as the protecting group. After the phthalimide compound has been formed, the protecting group is removed, for example, by hydrogenation to remove the benzyl group.

It will also be appreciated that $R_2$ and/or $R_3$ in the final products (I) include groups that may be sensitive to reaction in the process given above. Thus, where desired, one may use a precursor group for the final meanings of $R_2$ and/or $R_3$ in the appropriate starting materials. For example, the nitro group may be employed as a precursor for the amino group as a final meaning of $R_2$ and/or $R_3$. The nitro group can be converted to the amino group by catalytic hydrogenation. The amino group may itself be converted to the dimethylamino group by reaction with formaldehyde and formic acid.

The compounds of formula III and acids of formula IV are known compounds or, if new, accessible by known methods. The reaction of the amine of formula III with phthalic anhydride or its substitution product can be carried out in known manner. In some cases, it is found that the reaction product of the phthalic anhydride or its substitution product with the amine of formula III is a phthalic acid amide having the formula VI

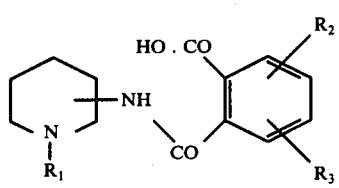
(VI)

In such cases the phthalimide formation can be completed by treatment of amide of formula IX with a dehydrating agent, for example, acetic anhydride.

If desired, a compound of formula I, where $R_1$ is lower alkyl, phenyl(lower)alkyl, pyridyl(lower)alkyl, furyl(lower)alkyl or thienyl(lower)alkyl, may be obtained by alkylation of a corresponding compound where $R_1$ is hydrogen. In particular compounds of the invention are accessible by forming an N-benzyl-piperidine compound of formula

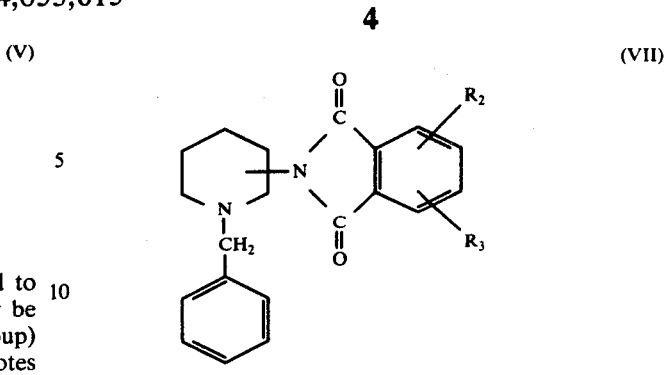
(VII)

by process step (a), subsequent debenzylation in known manner to form the compound of formula V, and if desired, alkylation to introduce a different group $R_1$.

The compounds of the invention may be used as chemical intermediates. Thus, for example, the phthalimido group of compounds of the formula (I) can be converted to an amino group by reaction with hydrazine or concentrated hydrochloric acid.

The compounds of formula V are also useful as intermediates for the preparation of compounds described in our U.K. Pat. Application No. 48593/72 and U.S. Pat. Application Ser. No. 334,799 (filed on Feb. 22, 1973 for "4-Aminoquinoline Derivatives" in the name of Archibald, Boyle and Saunders) now U.S. Pat. No. 3,875,165. The intermediates are used according to the following reaction scheme:

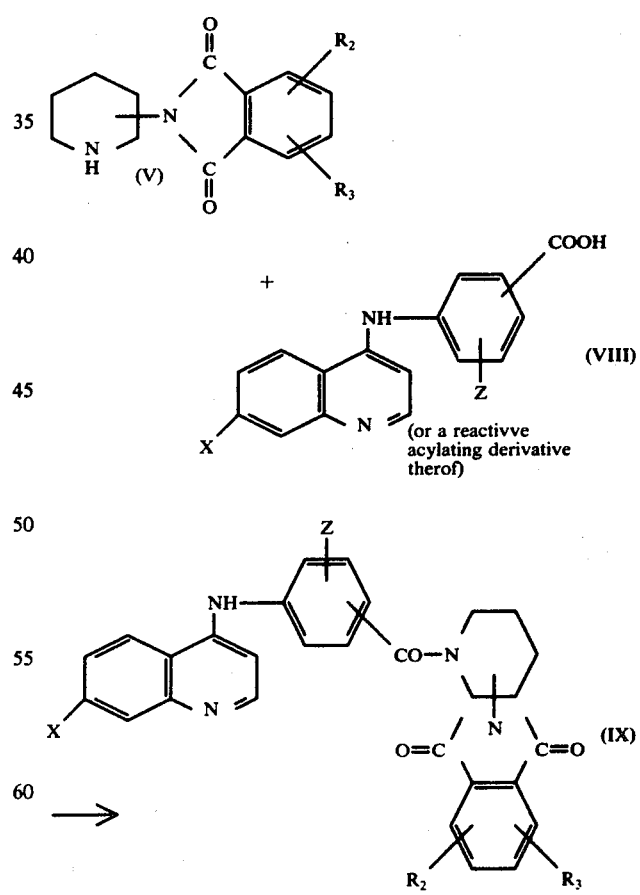

(where X is a halogen atom, for example, chlorine or bromine, or a trifluoromethyl group, Z is hydrogen or a substituent selected from, for example, lower alkyl, lower alkoxy, halogen, trifluoromethyl, nitro, amino and hydroxy and $R_2$ and $R_3$ are as defined above).

The compounds of formula I and their pharmaceutically suitable acid addition salts are also indicated for pharmacological usage. In particular they show anticonvulsant activity and, in some cases, also show anti-inflammatory activity or anti-arrhythmic activity, when tested on warm blooded animals. Anti-inflammatory activity is shown by 1-benzyl-4-phthalimido-piperidine and anti-arrhythmic activity is shown by 1-ethyl-3-phthalimido-piperidine and 1-ethyl-3-(4-nitrophthalimido)piperidine. 4-phthalimidopiperidine is active as an inhibitor of blood platelet aggregation.

The invention also includes pharmaceutical compositions containing as active ingredients a compound of formula (I) or a pharmaceutically acceptable acid addition salt thereof which may be micronised if desired. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredients in a unit dose of composition may be varied or adjusted from 5 mg. to 500 mg., according to the particular need and the activity of the active ingredient. The invention also includes the compounds in the absence of carrier where the compounds are in unit dosage form.

The following non-limiting Examples illustrate the invention:

EXAMPLE 1

1-Benzyl-4phthalimido-piperidine 16.8 Grams of phthalic anhydride and 21.6 grams of 4-amino-1-benzyl-piperidine were stirred together while they were being heated in an oil bath at 150° C for 30 minutes. On cooling, the resulting glassy solid was heated with 400 milliliters of methanol to give 26.5 grams of 1-benzyl-4-phthalimidopiperidine. Melting point: 154°–7° C.

ANALYSIS: Found: 75.4%C, 6.4%H, 8.9%N. $C_{20}H_{20}N_2O_2$ requires 75.0%C, 6.3%H, 8.7%N.

EXAMPLE 2

4-Phthalimido-piperidine 16.0 Grams of 1-benzyl-4-phthalimido-piperidine were dissolved in 200 milliliters of 50% methanol/acetic acid and 25 milliliters of ethereal hydrogen chloride, and were hydrogenated at 60° C and 60 psi in the presence of 2.0 grams of 10% palladium-on-charcoal catalyst. After 4 hours the reaction mixture was filtered while still hot and addition of ether gave 8.7 grams of 4-phthalimido-piperidine mono-hydrochloride. Melting point: 300° with decomposition.

ANALYSIS: Found: 58.4%C, 5.8%H, 10.5%N. $C_{13}H_{14}N_2O_2HCL$ requires 58.5%C, 5.7%H, 10.5%N.

EXAMPLE 3

1-Ethyl-3-phthalimido-piperidine 6.4 Grams of 3-amino-1-ethyl-piperidine and 7.4 grams of phthalic anhydride were heated together in an oil bath at 150° C for 20 minutes. On cooling, the resulting solid was recrystallized twice from methanol to give 4.2 grams of the title compound. Melting Point: 155° C.

ANALYSIS: Found: 70.0%C, 7.1%H, 11.1%N. $C_{15}H_{18}N_2O_2$ requires 69.7%C, 7.0%H, 10.9%N.

EXAMPLE 4

1-Ethyl-3-(4-nitrophthalimido)piperidine 6.40 Grams of 3-amino-1-ethylpiperidine in 150 milliliters of chloroform were added to a suspension of 9.65 grams of 4-nitrophthalic anhydride in 100 milliliters of chloroform. The solution formed was stirred at room temperature for twenty minutes and evaporated to dryness. The gummy residue was dissolved in 50 milliliters of acetic anhydride and the mixture was heated to 100° C for thirty-five minutes. The excess acetic anhydride was distilled and the residue extracted into 100 milliliters of chloroform and the solution was washed with 50 milliliters of saturated sodium bicarbonate solution, 50 milliliters of water, dried over magnesium sulphate and evaporated to give a brown oil. The oil was dissolved in 20 milliliters of isopropanol and ethereal hydrogen chloride was added to give 9.33 grams of the title compound as the hydrochloride, quarterhydrate.

Melting Point: >300° C. ANALYSIS: Found: C, 52.5%; H, 5.5%; N, 12.1%. $C_{15}H_{17}N_3O_4.HCL.1/4H_2O$ requires C, 52.5%; H, 5.4%; N, 12.2%.

EXAMPLE 5

1-Ethyl-3-(3-nitrophthalimido)piperidine

3-Nitrophthalic anhydride (0.01 moles) and 3-amino-1-ethylpiperidine (0.01 moles) are reacted in a similar manner to that described in Example 4 to give the title compound in the form of the hydrochloride. Melting Point: >300° C.

EXAMPLE 6

3-(4-Aminophthalimido)-1-ethylpiperidine 2.8 Grams of 1-ethyl-3-(4-nitrophthalimido)piperidine were dissolved in 50 milliliters of hot glacial acetic acid and were hydrogenated at 50° C and 50 p.s.i. in the presence of 0.1 grams of 5% palladium-on-charcoal catalyst until the theoretical amount of hydrogen was taken up. The hot solution was filtered and the mixture cooled and the solid formed was filtered and dried to give 1.06 grams of the title compound in the form of the monohydrochloride.

Melting Point: >300° C. ANALYSIS: Found: C, 57.9%, H, 6.5%; N, 13.5%. $C_{15}H_{19}N_3O_2.HCl$ requires C, 58.15%, H, 6.5%; N, 13.6%.

EXAMPLE 7

3-(3-Aminophthalimido)-1-ethylpiperidine 3.52 Grams of 1-ethyl-3-(3-nitrophthalimido)piperidine were hydrogenated in a similar manner so that described in Example 6 to give the title compound in the form of the monohydrochloride. Melting Point: >300° C.

ANALYSIS: Found: C, 58.4%, H, 6.5%; N, 13.5%. $C_{15}H_{19}N_3O_2.HCl$ requires C, 58.15%; H, 6.5%; N, 13.6%.

EXAMPLE 8

1-Ethyl-3-(3-methylphthalimido)piperidine

3-Amino-1-ethylpiperidine and 3-methylphthalic anhydride are reacted in a similar manner so that described in Example 3 to give the title compound.

EXAMPLE 9

1-Ethyl-3-(4-methylphthalimido)piperidine

3-Amino-1-ethylpiperidine and 4methylphthalic anhydride are reacted in a similar manner to that described in Example 3 to give the title compound.

EXAMPLE 10

3-(4-Dimethylaminophthalimido)-1-ethylpiperidine 3-(4-Aminophthalimido)-1-ethylpiperidine hydrochloride is heated on a steam-bath with formic acid and formaldehyde for 5 hours. The volatile material is evaporated off, and the residue is dissolved in water, basified and extracted into ether. Evaporation of the ether solution gives the title compound.

EXAMPLE 11

1-n-Butyl-4-(3,6-dichlorophthalimido)piperidine

4-Amino-1-n-butylpiperidine and 3,6-dichlorophthalic anhydride are reacted in a similar manner so that described in Example 3 to give the title compound.

EXAMPLE 12

1-n-Butyl-4-(4-nitrophthalimido)piperidine 4.69 Grams of 4-amino-1-n-butylpiperidine in 100 milliliters of chloroform were added to a suspension of 5.79 grams of 4-nitrophthalic anhydride in 75 milliliters of chloroform and the solution was evaporated to dryness. 40 milliliters of acetic anhydride were added and the mixture was then heated on a steam bath for half an hour. The excess acetic anhydride was evaporated off and the residue dissolved in 40 milliliters of methanol and ethereal hydrogen chloride was added to give a solid which was collected giving 2.50 grams of the title compound as the monohydrochloride.

Melting Point: 260° C. ANALYSIS: Found: C, 55.19%; H, 6.19%; N, 11.3%. $C_{17}H_{21}N_3O_4.HCl$ requires C, 55.5%; H, 6.0%; N, 11.4%.

EXAMPLE 13

4-(4-Aminophthalimido)-1-n-butylpiperidine

To a solution of 1.2 grams of 1-n-butyl-4(4-nitrophthalimido piperidine monohydrochloride in 50 milliliters of glacial acetic acid were added 0.3 grams of 5% palladium on carbon catalyst and the mixture hydrogenated at 40°-60° C at 50 p.s.i. until the theoretical amount of hydrogen was taken up. The solution was cooled, filtered over kieselguhr and evaporated to a small volume, then triturated with ether to give the title compound as the monohydrochloride. Melting Point: 265°-270° C.

ANALYSIS: Found: C, 59.6%; H, 7.3%; N, 12.2%. $C_{17}H_{23}N_3O_2.HCl$ requires C, 59.6%; H, 7.2%; N, 12.3%.

EXAMPLE 14

1-Cyclohexyl-4-(4-nitrophthalimido)piperidine 6.85 Grams of 4-amino-1-cyclohexylpiperidine were added to 7.26 grams of 4-nitrophthalic anhydride in 100 milliliters of chloroform and the solution was evaporated to dryness. 50 millilters of acetic anhydride were then added and the solution was heated on a steam bath for half an hour. The excess acetic anhydride was evaporated off and the residue dissolved in 40 millilters of isopropyl alcohol and the product crystallised out. This was filtered, dried and dissolved in the least amount of ethanol and ethereal hydrogen chloride added to give 2.85 grams of the title compound which was collected as the monohydrochloride. Melting Point: 265°-270° C.

ANALYSIS: Found: C, 58.0%; H, 6.31%; N, 10.5%. $C_{19}H_{23}N_3O_4.HCl$ requires C, 57.9%; H, 6.14%; N, 10.7%.

EXAMPLE 15

1-Benzyl-4-(4-nitrophthalimido)piperidine 9.51 Grams of 4amino-1-benzylpiperidine and 9.66 grams of 4-nitrophthalic anhydride were reacted in a similar manner so that described in Example 14 to give 9.19 grams of the title compound as the monohydrochloride quarterhydrate. Melting Point: 240°-2° C.

ANALYSIS: Found: C, 58.8%; H, 5.3%; N, 9.95%. $C_{20}H_{19}N_3O_4.HCl.1/4H_2O$ requires C, 59.1%; H, 5.1%; N, 10.3%.

EXAMPLE 16

4-(4-Aminophthalimido)-1-benzylpiperidine 3.3 Grams of 1-benzyl-4-(4-nitrophthalimido)piperidine monohydrochloride quarterhydrate were reduced in a similar manner so that described in Example 13 to give 1.25 grams of the title compound as the monohydrochloride quarterhydrate. Melting Point: 216°-8° C.

ANALYSIS: Found: C, 63.5%; H, 6.3%; N, 11.15%. $C_{20}H_{21}N_3O_2.HCl.1/4H_2O$ requires C, 63.1%; H, 6.1%; N, 11.0%.

EXAMPLE 17

4-(4-Nitrophthalimido)-1-(2-phenylethyl)piperidine 9.66 Grams of 4-nitrophthalic anhydride and 10.11 grams of 4-amino-1-(2-phenylethyl)piperidine were reacted in a similar manner to that described in Example 12 to give 10.51 grams of the title compound as the monohydrochloride.

Melting Point: 240°-2° C. ANALYSIS: Found: C, 60.9%; H, 5.5%; N, 10.0%. $C_{21}H_{21}N_3O_4.HCl$ requires C, 60.6%; H, 5.33%; N, 10.1%.

EXAMPLE 18

4-(4-Chlorophthalimido)-1-(2phenethyl)piperidine

To 5.48 grams of 4-chlorophthalic anhydride was added 5.70 grams of 4-amino-1-(2-phenylethyl)piperidine and the mixture stirred and heated to 150° C for half an hour. The product was dissolved in isopropyl alcohol and ethereal hydrogen chloride added to give a solid which was collected giving 2.52 grams of the title compound as a monohydrochloride hemi-hydrate. Melting Point: 232°-3° C.

ANALYSIS: Found: C, 61.0%; H, 5.5%; N, 6.7%. $C_{21}H_{21}ClN_2O_2.HCl.\frac{1}{2}H_2O$ requires C, 60.7%; H, 5.8%; N, 6.7%.

EXAMPLE 19

4-(4-Nitrophthalimido)-1-(3-pyridylmethyl)piperidine a. 52.06 Grams of 3-aminomethylpyridine was refluxed with 200 milliliters of methyl acrylate for 96 hours. The excess methyl acrylate was evaporated off to give 137.6 grams of 3-[N,N-di(2-methoxycarbonylethyl)aminomethyl] pyridine.

b. 72 Grams of sodium hydride (50% dispersion in oil) were added to 1.5 liters of sodium dried benzene and the suspension formed were refluxed. 137.61 grams of 3-[N,N-di(2-methoxycarbonylethyl)aminomethyl]pyridine were added dropwise to the refluxing sodium hydride suspension in benzene and the solution was heated for a further 2½ hours. 500 milliters of concentrated hydrochloric acid was added carefully. The mixture was filtered, separated and the acid layer combined with a further 200 milliliters of concentrated hydrochloric acid and refluxed for 18 hours. Solid sodium carbonate was added till the solution had a pH of 8. The mixture was filtered and the solution treated with benzene. The benzene extracts were combined, dried over magnesium sulphate and the solvent was evaporated to give 66.58 grams of N-(3-pyridylmethyl)-4-piperidone.

c. 38.05 Grams of N-(3-pyridylmethyl)-4-piperidone and 27.8 grams of hydroxylammonium hydrochloride were dissolved in 600 milliliters of ethanol. 300 milliliters of 30% sodium hydroxide were added and the solution refluxed for half an hour, and then 40 grams of nickel, aluminium alloy were carefully added portionwise to the refluxing solution. The solution was refluxed for a further 3 hours, cooled and filtered through kieselguhr. The solution was evaporated and the residue treated with ether. The combined ether extracts were dried over magnesium sulphate and evaporated to give 33.72 grams of 4-amino-N-(3-pyridylmethyl)piperidine.

d. 9.6 Grams of 4-amino-N-(3-pyridylmethyl)piperidine were dissolved in 100 milliliters of chloroform and 9.65 grams of 4-nitrophthalic anhydride were added and the mixture was stirred for half an hour. The chloroform was evaporated off and 200 milliliters of acetic anhydride were added. The mixture was heated on a steam bath for half an hour and then evaporated to dryness. The residue was washed with isopropyl alcohol which was evaporated off. The residue was triturated with ether to give 15.38 grams of yellow solid. This was dissolved in the least amount of ethanol and to it was added ethereal hydrogen chloride to give a precipitate. Sodium carbonate solution was added until the precipitate dissolved and the solution was then treated with chloroform. The chloroform extracts were combined, dried over magnesium sulphate and evaporated down to give 7.42 grams of the title compound. Melting Point: 143°-4° C.

ANALYSIS: Found: C, 60.9%; H, 5.08%; N, 14.5%. $C_{19}H_{18}N_4O_4.\frac{1}{2}H_2O$ requires C, 60.8%; H, 5.10%; N, 14.9%.

EXAMPLE 20

1-Furfuryl-4-(4-nitrophthalimido)piperidine a. 48.56 Grams of furfurylamine and 200 milliliters of methyl acrylate are refluxed together for 84 hours. The excess methyl acrylate is evaporated off to give 133.46 grams of N,N-di(2-methoxycarbonylethyl)furfurylamine.

b. 65.36 Grams of N,N-di(2methoxycarbonylethyl)-furfurylamine are added dropwise to a refluxing solution of 42 grams of sodium hydride (50% dispersion in oil) in 0.75 liters of sodium dried benzene. A few milliliters of ethanol are added to start the reaction and the solution is refluxed for 2½ hours. 600 milliliters of water are added and the benzene water mixture separates. The aqueous solution is brought to pH7 with 2N hydrochloric acid and the solution is evaporated to give a brown residue. This is dissolved in methanol, filtered and the solution is evaporated. The residue is dissolved in absolute ethanol, filtered and the solution evaporated. The brown residue is triturated with ether to give 25 grams of the sodium salt of 3-carboxy-N-furfuryl-4-piperidine. On decarboxylation by heating in solution in a suitable solvent this sodium salt gives N-(2-furfuryl)4-piperidone.

c. N-(2-Furfuryl)-4-piperidone is reacted with hydroxylamine, followed by nickel, aluminium alloy in 30% sodium hydroxide solution in a similar manner to that described in Example 19 to give 4-amino-N-(2-furfuryl)piperidine.

d. 4-Amino-N-(2-furfuryl)piperidine and 4-nitrophthalic anhydride are reacted in a similar manner to that described in Example 15 to give the title compound.

EXAMPLE 21

N-(2-Thienylmethyl)-4-(4-nitrophthalimino)piperidine a. 2-Aminomethylthiophene and methyl acrylate are reacted in similar manner so that described in Examples 19 to give 2-[N,N-di(methoxycarbonylmethyl)aminomethyl]thiophene. b. 2-[N,N-Di(methoxycarbonylethyl)aminomethyl]thiophene is cyclized and decarboxylated in a similar manner to that described in Example 19 to give N-(2thienylmethyl)-4-piperidine.

c. N-(2-Thienylmethyl)-4-piperidone is reacted with hydroxylamine, followed by nickel, aluminium alloy in 30% sodium hydroxide solution, in a similar manner to that described in Example 19 to give 4-amino-N-(2-thienylmethyl)piperidine.

d. 4-Amino-N-(2-thienylmethyl)piperidine and 4-nitrophthalic anhydride are reacted in a similar manner to that described in Example 15 to give the title compound.

EXAMPLE 22

1-Ethyl-4-phthalimido-piperidine 4.74 Grams (0.032 mole) of 4-amino-N-ethylpiperidine and 5.5 grams (0.032 mole) of phthalic anhydride were dissolved in 150 milliliters of chloroform and the solution was stirred for an hour at room temperature. The solvent was evaporated off and the solid dissolved in 100 milliliters of acetic anhydride and the solution was refluxed for an hour. The acetic anhydride was evaporated off and the residue dissolved in isopropyl alcohol and ethereal hydrogen chloride was added drop by drop until the solution was slightly acidic. A solid crystallized and was collected and washed with isopropyl alcohol and dried to give 5.3 grams of the hydrochloride of the title compound, m.p. 266°–268° C.

ANALYSIS $C_{15}H_{18}N_2O_2.HCl$ requires C, 61.1%; H, 6.49%; N, 9.50%. Found: C, 60.9%; H, 6.75%; N, 9.29%.

EXAMPLE 23

1-Ethyl-4-(4-nitrophthalimido)piperidine 6.50 Grams (0.05 mole) of 4-amino-N-ethyl piperidine and 9.65 grams (0.05 mole) of 4-nitrophthalic anhydride were dissolved in 150 milliliters of chloroform and the solution was stirred for an hour at room temperature. The chloroform was evaporated and the solid dissolved in 50 milliliters of acetic anhydride and the solution was refluxed for an hour. The acetic anhydride was evaporated off and the dark red residue treated with isopropyl alcohol and the solvent evaporated. The residue which was a gum was repeatly subjected to treatment with isopropyl alcohol and evaporation of the solvent until a crystalline solid was produced. The solid was taken up in chloroform and this was washed with sodium bicarbonate solution, then water and then brine until the aqueous layer was neutral. The chloroform extract was dried with magnesium sulphate, filtered and evaporated to give a solid. Microanalysis showed this to be impure and the bicarbonate washing was repeated as outlined above. The dried chloroform extract was evaporated off and the residue treated with ether to give 2.5 grams of the title compound as a yellow solid, m.p. 153°–155°.

ANALYSIS, $C_{15}H_{17}N_3O_4$ requires C, 59.4% H, 5.65%; N, 13.9%; Found: C, 59.2%; H, 5.66%; N, 13.7%.

EXAMPLE 24

4-(4-Aminophthalimido)-1-ethylpiperidine

A solution of 1.7 grams (0.005 mole) of 1-ethyl-4-(4-nitrophthalimido)piperidine hydrochloride in 60 milliliters of glacial acetic acid was hydrogenated over 0.1 grams of 10% palladium on carbon catalyst at 50 p.s.i. After the theoretical uptake of hydrogen, a little acetic acid/ethanol mixture was added to dissolve precipitated solid; the catalyst was filtered off, the solvents evaporated and the residue trituated with ether to give a yellow solid. Recrystallisation from methanol gave 1.18 grams of 4-(4-aminophthalimido)-1-ethylpiperidine hydrochloride hydrate, m.p. 254° C(decomp).

Analysis: Found C, 54.8%; H, 6.3% N,12.8% $C_{15}H_{19}N_3O_2.HCl.H_2O$ requires C, 55.0%; H, 6.75; N, 12.8%

Compounds can be tested for anti-convulsant activity by the following two procedures:

PROCEDURE A

ANTI-PENTYLENETETRAZOLE ACTIVITY

Procedures

Compounds at a number of dose levels are administered p.o. to groups of six mice (3 males and 3 females). One hour later the animals are challenged with pentylenetetrazole (125mg/kg i.p.). The incidence of clonic and tonic convulsions and deaths is observed for one-half hour. Protection against convulsions and death is determined by comparison with controls run simultaneously. An $ED_{50}$ against convulsions is calculated from probit-log dose curves.

PROCEDURE B

MAXIMAL ELECTROSHOCK SEIZURES (MES)

Procedure

Compounds at graded dose levels are administered orally to groups of six mice. One hour later, the animals are given a supramaximal electroshock through pinna electrodes (25 mA, 0.2 sec). Presence or absence of tonic extensor seizures as well as the number of deaths are recorded.

The percent protection against seizures is calculated. An $ED_{50}$ against convulsions is calculated from probit-log dose curves.

A compound is regarded as inactive in either one of the two procedures if the $ED_{50}$ of the compound in the test procedure is greater than 400 mg/kg. If a compound is active in either procedure the $ED_{50}$ is normally quoted as one of the following ranges:- less than 1 mg/kg, 1–5 mg/kg, 6–15 mg/kg, 16–30 mg/kg, 31–50 mg/kg, 51–100 mg/kg, 101–200 mg/kg and 201–400 mg/kg.

The closest prior art known to the Applicants is U.S. Pat. No. 3,316,276 which discloses a class of N-(3-pyrrolidinyl)phthalimide derivatives including N-(1-ethyl-3-pyrrolidinyl)-phthalimide, which may alternatively be called 1-ethyl-3-phthalimidopyrrolidine. A sample of 1-ethyl-3-phthalimidopyrrolidine has been prepared and tested in Procedures A and B described above. The results obtained are compared in the following table with those of the nearest compound of the invention

TABLE

| COMPOUND | $ED_{50}$ Procedure A | Procedure B |
|---|---|---|
| 1-ethyl-3-phthalimido- | >400 mg/kg | >400 mg/kg |

TABLE-continued

| COMPOUND | ED$_{50}$ Procedure A | Procedure B |
|---|---|---|
| pyrrolidine | (INACTIVE) | (INACTIVE) |
| 1-ethyl-3-phthalimido-piperidine | 51-100 mg/kg | 31-50 mg/kg |

The preferred compounds of the invention are those having the formula

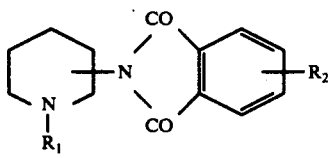

where $R_1$ is selected from lower alkyl and benzyl and $R_2$ is selected from nitro and amino and their pharmaceutical acceptable acid addition salts. In particular the phthalimidopiperidine products of Examples 4, 6, 12, 13, 15 and 16 showed ED$_{50}$ values in the ranges of about 6-15 mg/kg, when tested in Procedures A described above, and showed ED$_{50}$ values within the ranges 1-5 mg/kg, 6-15 mg/kg and 15-30 mg/kg, when tested in Procedure B described above.

We claim:

1. A compound selected from those having the formula

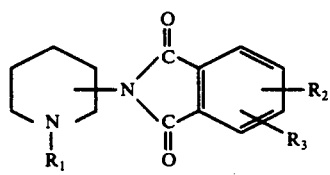

and their pharmaceutically acceptable acid addition salts, wherein $R_1$ is selected from the group consisting of hydrogen, lower alkyl, cycloalkyl of 5 to 7 carbon atoms, phenyl(lower)alkyl, pyridyl(lower)alkyl, furyl(lower)alkyl and thienyl(lower)alkyl, and $R_2$ and $R_3$ are independently selected from the group consisting of hydrogen, halogen, lower alkyl, nitro, amino and di(-lower alkyl)amino.

2. A compound selected from those having the formula

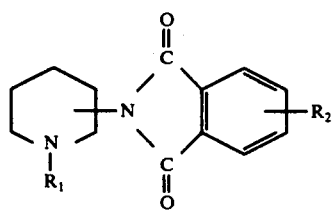

and their pharmaceutically acceptable acid addition salts, wherein $R_1$ is selected from lower alkyl and benzyl and $R_2$ is selected from nitro and amino.

3. A compound as defined in claim 1, which is 1-benzyl-4-phthalimidopiperidine or a pharmaceutically acceptable acid addition salt thereof, 4. A compound as defined in claim 1, which is 4-phthalimido-piperidine or a pharmaceutically acceptable acid addition salt thereof.

5. A compound as defined in claim 1, which is 1-ethyl-3-phthalimido-piperidine or a pharmaceutically acceptable acid addition salt thereof.

6. A compound as defined in claim 2, which is 1ethyl-3-(4nitrophthalimido)piperidine or a pharmaceutically acceptable acid addition salt thereof.

7. A compound as defined in claim 1, which is 1ethyl-3-(3-nitrophthalimido)piperidine or a pharmaceutically acceptable acid addition salt thereof.

8. A compound as defined in claim 2, which is 3-(4-aminophthalimido)-1-ethylpiperidine or a pharmaceutically acceptable acid addition salt thereof.

9. A compound as defined in claim 1, which is 3-(3-aminophthalimido)-1-ethylpiperidine or a pharmaceutically acceptable acid addition salt thereof.

10. A compound as defined in claim 2, which is 4-(4-aminophthalimido)-1-n-butylpiperidine or a pharmaceutically acceptable acid addition salt thereof.

11. A compound as defined in claim 1, which is 1-cyclohexyl-4-(4nitrophthalimido)piperidine or a pharmaceutically acceptable acid addition salt thereof.

12. A compound as defined in claim 2, which is 1-n-butyl-4-(4-nitrophthalimido)piperidine or a pharmaceutically acceptable acid addition salt thereof.

13. A compound as defined in claim 1, which is 4-(4nitrophthalimido)-1-(3-pyridylmethyl) piperidine or a pharmaceutically acceptable acid addition salt thereof.

14. A compound as defined in claim 1, which is 4-(4-chlorophthalimido)-1-(2-phenethyl)piperidine or a pharmaceutically acceptable acid addition salt thereof.

15. A compound as defined in claim 2, which is 1-benzyl-4(4-nitrophthalimido)piperidine or a pharmaceutically acceptable acid addition salt thereof.

16. A compound as defined in claim 2, which is 4-(4-aminophthalimido)-1-benzylpiperidine or a pharmaceutically acceptable acid addition salt thereof.

17. A compound as defined in claim 1, which is 4-(4-nitrophthalimido)-1-(2-phenylethyl)-piperidine or a pharmaceutically acceptable acid addition salt thereof.

18. A compound as defined in claim 1, which is 1-ethyl-4-phthalimido-piperidine or a pharmaceutically acceptable acid addition salt thereof.

19. A compound as defined in claim 1, which is 1-ethyl-4-(4-nitrophthalimido)piperidine or a pharmaceutically acceptable acid addition salt thereof.

20. A compound as defined in claim 1, which is 4-(4-nitrophthalimido)piperidine or a pharmaceutically acceptable acid addition salt thereof.

21. An anti-convulsant composition comprising an anti-convulsantly effective amount of a compound as claimed in claim 1 and a pharmaceutically tolerable carrier.

* * * * *